United States Patent [19]
Foster

[11] Patent Number: 5,485,277
[45] Date of Patent: Jan. 16, 1996

[54] SURFACE PLASMON RESONANCE SENSOR AND METHODS FOR THE UTILIZATION THEREOF

[75] Inventor: Mark W. Foster, Torrance, Calif.

[73] Assignee: Physical Optics Corporation, Torrance, Calif.

[21] Appl. No.: 280,475

[22] Filed: Jul. 26, 1994

[51] Int. Cl.$^6$ .................................................. G01N 21/17
[52] U.S. Cl. ............................................................ 356/445
[58] Field of Search ............................................. 356/445

[56] References Cited

U.S. PATENT DOCUMENTS

| | | | |
|---|---|---|---|
| 3,939,350 | 2/1976 | Kronick et al. | 356/36 |
| 4,844,613 | 7/1989 | Batchelder | 356/318 |
| 5,007,210 | 4/1991 | Eigler et al. | |
| 5,064,619 | 11/1991 | Finlan | 356/445 |
| 5,216,244 | 6/1993 | Esaki et al. | 356/244 |
| 5,313,264 | 5/1994 | Ivarsson et al. | 356/446 |

OTHER PUBLICATIONS

Raether, H., Surface Plasmons on Smooth and Rough Surfaces and on Gratings, Springer–Verlag, Berlin (1988).
Hage, D. S. "Immunoassays," Anal. Chem., 63(12), (1991), pp. 206R–209R (15 Jun. 1991).
Sadowski, J. W., "Review of Optical Methods in Immunosensing," SPIE Proc. vol. 954, pp. 413–419 (1988) (no month).
Wolfbeis, O., ed., Fiber Optic Chemical Sensors and Biosensors, vol. II, CRC Press, Boston, (1991), 217–257 chapter 17 (no month).
Kwok, S., D. H. Mack, K. B. Mullins, B. Poiesz, G. Ehrlich, D. Blair, A. Friedman–Kien, and J. J. Sninsky "Identification of Human Immunodeficiency Virus Sequences by Using In Vitro Enzymatic Amplification and Oligmer Clevage Detection," J. Virol., 61, (1987), pp. 1690–1694 (May 1987).
Golden, J. P. et al., "Fluorometer and Tapered Fiber Optic Probes for Sensing in the Evanescent Wave," Opt. Eng., 31(7), 1992, pp. 1458–1462 (Jul. 1992).
Pharmacia Biacore™ product brochure (no date).
ICN Immunobiologicals Catalog, May 1992, pp. 732–735.
Harlow, E. and D. Lane, Antibodies: A Laboratory Manual, Cold Spring Harbor Laboratory, Cold Spring Harbor (1988) chapters 2 and 14. (no month).
Lambeck, P. V., "Integrated Opto–Chemical Sensors," Sens. Actu. B, 8, 1992,. pp. 103–116 (no month).
Mujumdar, R. B., et al., Cytometry, 10, 1989, pp. 11–19 (no month).
Ernst, L. A., et al., Cytometry, 10, 1989, pp. 10–13 (no month).
Southwick, P. L. et al., Cytometry, 11, 1990, pp. 418–430 (no month).
Daneshvar, M. I., "Investigation of a Near–Infrared Fiber Optic Immunosensor," Proceedings SPIE, 2068, Chemical, Biochemical, and Environmental Sensors V, R. A. Lieberman (ed), 1993, pp. 128–138 (no month).
Morgan, H. and D. M. Taylor, "A Surface Plasmon Resonance Immunosensor Based on the Streptavidin–Biotin Complex," Biosens. & Bioelect., 7, (1992), pp. 405–410 (no month).

(List continued on next page.)

Primary Examiner—Richard A. Rosenberger
Attorney, Agent, or Firm—Nilles & Nilles

[57] ABSTRACT

A surface plasmon resonance sensor including: a substrate-mode metal film coated waveguide cartridge including: a planar waveguide including a plurality of reflector surfaces within the planar waveguide; and a metal film deposited directly on the planar waveguide, the metal film and the planar waveguide defining a plasmon resonance interface directly on the planar waveguide; a sample flow cell adjacent the substrate-mode metal film coated waveguide cartridge; a transverse magnetic polarized light source optically connected to the planar waveguide; a cylindrical diverging lens optically connected to the planar waveguide; and a detector array comprising a plurality of photodetectors optically connected to the cylindrical diverging lens. Methods of using the surface plasmon resonance sensor are also disclosed.

20 Claims, 10 Drawing Sheets

OTHER PUBLICATIONS

Taylor, D. M., et al., "Characterization of Chemisorbed Monolayers by Surface Potential Measurements," J. Phys. D:Appl. Phys., 124, (1991), pp. 443–450 (no month).

Kobayashi, J. and Y. Ikada, "Covalent Immobilization of Proteins Onto the Surface of Poly(vinyl alcohol) Hydrogel," Biomaterials, 12, (1991), pp. 747–751 (Oct. 1991).

Johnsson, B. et al., "Immobilization of Proteins to a Carboxymethyldextran–Modified Gold Surface for Biospecific Interaction Analysis in Surface Plasmon Resonance Sensors," Anal. Biochem., 196, (1991), 268–277 (no month).

Lofas, S. and B. Johnsson, "A Novel Hydrogel Matrix on Gold Surfaces in Surface Plasmon Resonance Sensors for Fast and Efficient Covalent Immobilization of Ligands," J. Chem. Soc. Commun., (1990), pp. 1526–1528 (no month).

SURFACE PLASMON RESONANCE SENSOR AND METHODS FOR THE UTILIZATION THEREOF

FIELD OF THE INVENTION

The present invention relates generally to the field of surface plasmon resonance sensors. More particularly, the present invention relates to planar waveguide surface plasmon resonance biosensors and methods for the utilization thereof.

BACKGROUND OF THE INVENTION

Within this application several references are referenced by arabic numerals within parentheses. Full citations for these publications may be found at the end of the specification immediately preceding the claims. The disclosures of all of these references in their entireties are hereby expressly incorporated by reference into the present application.

Many of the basic electronic properties of metals can be described by modeling them as condensed matter plasmas. Their electrons behave as a high density gas in a lattice of fixed positive charges. In this analogy, longitudinal density fluctuations, (i.e., plasma oscillations), can propagate through the volume of the metal. These oscillations, "volume plasmons," are quantized with an energy $hw_p$ where $w_p$ is the plasma frequency of the metal:

$$\omega_p^2 = \frac{4\pi n e^2}{m_e} \quad (1a)$$

where n is the volume electron density, e is the electron charge, and $m_e$ is the electron mass. The permittivity of a metal ($\epsilon_m$) is a function of its plasma frequency and electron damping. It generally has the complex form $\epsilon_m(\omega_p) = \epsilon_{re}(\omega_p) + i\epsilon_{im}$, where the imaginary component is related to the damping in the metal.

Electrons at the surface of a plasma behave somewhat differently from the "volume" electrons in the center of a plasma, due to the discontinuity at the interface. They still, however, exhibit coherent density fluctuations, which are known as surface plasmon oscillations. Surface plasmons can only exist at the interface between a metal film ($\epsilon_m$), 10, and a dielectric film ($\epsilon_d$), 20, as shown in FIG. 1(a). The magnitude of the electric field of these charge fluctuations, shown in FIG. 1(b), is a maximum at the interface (z=0) and decays exponentially away from the surface. The wave propagates along the interface in the x-direction with a wave vector whose magnitude is $k_{sp}=2\pi/\lambda_{sp}$, where $\lambda_{sp}$ is the wavelength of the surface plasmon oscillation and $h\omega_{spp}$ is the quantized energy of the excitation. FIG. 1(a) illustrates a metal/dielectric interface that supports surface plasmon waves and the exponential decay of the electric field distribution:

$$E = E_0 \exp[i(k_{sp}x \pm k_z z - \omega_{spp}t)] \quad (1b)$$

here + indicates z≥0, − indicates z<0, and $k_z$ is imaginary.

Surface plasmons are only one variety of many possible elementary quantized excitations of solid state matter, such as phonons, polaritons, excitons, and magnons. A polariton is defined as the coupled state between a photon and an excitation quantum. As the name polariton implies, these "quasiparticles" can only be excited using polarized light. A surface plasmon polariton (SPP) is the coupling of oscillating surface charge density with an electromagnetic field. Since surface plasmon waves propagate in a TM (transverse magnetic) mode, TM-polarized light will excite SPPs. Reference (1) discusses many of these properties in detail. The dispersion relation for the surface plasmon mode is a function of the permittivities of the metal ($\epsilon_m$) and dielectric materials ($\epsilon_d$) at the interface. The surface plasmon wave vector ($k_{sp}$) is defined by the dispersion relation as:

$$k_{sp} = \frac{\omega_{spp}}{c} \sqrt{\frac{\epsilon_m \epsilon_d}{\epsilon_m + \epsilon_d}} \quad (2)$$

where c is the speed of light in vacuum. Incident light cannot couple directly to surface plasmons on smooth surfaces since the real part of the radical in Eq. (2) is always greater than unity. Several techniques exist to excite to surface plasmons, such as electron beam bombardment, grating coupling, and total internal reflection (hereinafter, TIR) prism coupling.

If light is incident on the internal surface of a prism, 30, at an angle greater than the critical angle for total internal reflection, as shown in FIGS. 2(a) and 2(b), an evanescent wave is produced below the reflecting surface, 32, of the prism, 30. The evanescent wave decays exponentially in the direction normal to the prism surface, 32, (into the metal film, 10, / dielectric film, 20, bilayer) and has a dispersion relation given by:

$$k_x = n_p \frac{\omega}{c} \sin\theta \quad (3)$$

where $n_p$ is the refractive index of the prism, ω is the frequency of the incident light, θ is the incidence angle of light on the surface of the prism, and c is the speed of light in vacuum. For this technology, the prism is replaced by a novel "substrate" mode waveguide. The evanescent field dispersion relation at the reflecting interface is the same as Eq. (3), with $n_p$ replaced by $n_{wvg}$, the index of refraction of the waveguide.

FIG. 2(a) illustrates surface plasmon resonance through prism coupling. FIG. 2(b) illustrates reflectance near plasmon excitation. The resonant condition where the curves intersect, i.e. $k_x=k_{sp}$ and $hw=h\omega_{spp}$, is analytically described by combining the surface plasmon dispersion relation, Eq. (2) and Eq. (3) to give:

$$n_p \sin\theta_{sp} = \sqrt{\frac{\epsilon_m \epsilon_d}{\epsilon_m + \epsilon_d}} \quad (4)$$

which shows that the index of refraction of the prism and the permittivities of the thin film layers determine the incidence angle for which surface plasmon polaritons can be excited.

FIG. 2(b) shows schematically the reflected intensity of TM-polarized light from the prism as a function of incidence angle. The dip in reflectance is due to the absorption of energy from the evanescent wave by surface plasmons. Coupling of the light from the prism to the SPPs attenuates the amount of light totally internally reflected from the prism and dissipates it in the metal film as thermal energy. The phenomenon is strongest for incidence angle $\theta_{sp}$, where maximum coupling occurs and the reflectivity is nearly zero. At a typical interface, surface plasmons propagate approximately 10 μm before their energy is dissipated as heat. This short propagation length enables highly localized sensing. The nature of the resonance shown in FIG. 2(b) is revealed by analytically solving for reflectivity. By so doing, the Lorentzian nature of the plasmon resonance is revealed:

$$R = 1 - \frac{4\Gamma_i \Gamma_{rad}}{[k_x - (k_{sp} + \Delta k_z)]^2 + (\Gamma_i + \Gamma_{rad})^2} \quad (5)$$

where $\Gamma_i=\text{Im}(k_{sp})$, $\Gamma_{rad}=\text{Im}(\Delta k_x)$, $\Delta k_x=f(\epsilon_m, \epsilon_d, t_i)$, and $t_i$ is the thickness of the metal thin film layer in the structure. See reference (10). Eq. (5) reveals that the thickness of the metal film determines the depth of the resonance by the minimum condition $\Gamma_i=\Gamma_{rad}$. Only for one particular film thickness will the resonance completely attenuate the incident TM polarized light at the excitation angle $\theta_{sp}$.

The previous discussion elucidates two fundamental mechanisms by which surface plasmons can be used for sensing: the first is to fix the angle of incidence of TM-polarized light at $\theta_{sp}$ so that virtually no light will be transmitted. If the permittivity of one of the layers (e.g. the dielectric layer) is varied, the angular position of the plasmon resonance minimum shifts and the amount of transmitted light increases; second, if the thickness of one of the layers is varied, the efficiency of the coupling is modulated and the transmitted light again increases. By incorporating a dielectric transducing layer whose permittivity and/or thickness varies in response to analytes of interest, the surface plasmon multilayer can become a sensor.

Immunoassays and nucleic acid (DNA/RNA) probes are analytical techniques that use antibody-related reagents and nucleic acid hybridization, respectively, for the selective determination of sample components. For immunoassay, by monitoring the amount of antibody-to-antigen binding that occurs for a fixed amount of antigen or antibody, the concentrations of target analytes are determined. With nucleic acid probes, monitoring the selective binding (hybridization) of target DNA or RNA with genetic probes allows determination of the amount of target analyte. These techniques have the advantage of high selectivity, low detection limits, and compatibility with use in complex samples such as urine and blood, or soil samples in the case of bioagent detection. Immunoassay and detection technologies based on radiometric, enzymatic, surface acoustic wave, and optical means have been investigated for many years. See references (2, 3). Of these, optical techniques promise greater sensitivity, lower detection limits, and higher flexibility. Immunoassay and nucleic acid probe detection based on such optical techniques as attenuated total reflection (hereinafter, ATR), surface plasmon resonance (hereinafter, SPR), fluorescence, and bio/chemiluminescence have been studied and commercial immunosensors based on some of these techniques are beginning to appear. See references (4, 5).

The optical techniques are differentiated by whether they use direct or indirect sensing methods. Indirect biosensing uses secondary labels that are attached to the analyte of interest in a separate step, before binding, to differentiate between specific and non-specific binding events. Optical labels include organic fluorophores and bio/chemiluminescent molecules. These labels emit light whose intensity is quantified as a measure of the amount of analyte present. If no tagged analytes are present then, theoretically, no signal is measured. In the case of fluorescence immunoassay, an external source is required to cause the labels to fluorescence. This has several disadvantages since the excitation light must be kept very stable and strongly post filtered in order to achieve high sensitivity. For low analyte levels (corresponding to low fluorescent light levels) the background of the excitation light that makes it through the filter (none are 100% efficient) can exceed the low level fluorescent signals, thus limiting the lower detection limit of a fluorescence biosensor. Direct biosensing involves measuring the direct antigen/antibody binding, or DNA/RNA hybridization, without the use of any secondary labels. Because of this, direct techniques promise more rapid screening times due to the reduced number of assay steps, and commensurate reduction in operator skill, required to perform reliable tests. Though the direct techniques (ATR and SPR) promise more rapid screening by reducing immunoassay steps, they can suffer from interference by non-specific binding in the presence of proteins or other interferents.

Immunoassay biosensors monitor the specific binding that occurs between antibodies and antigens. Antibodies are simply proteins produced by the lymphocytes of higher animals in response to the presence of foreign molecules (antigens). These proteins have been synthesized for a wide variety of antigens by introducing the antigen into a host and isolating the corresponding antibodies produced by the lymphocytes in the host's immune system. See reference (6). More recently, the production of large amounts of specific antibodies by genetically engineered microorganisms has been reported. Sensitive immunological detection of both biological and chemical materials has been demonstrated. See reference (7).

Because each immunological binding event involves two different molecules, immunoassay can be used to perform two primary tasks: detection of antibodies using antigens, and detection of antigens using antibodies. The detection of antibodies is of primary interest in biomedical diagnostics, where the presence of antibodies associated with a particular disease, bacteria, or virus indicates the presence of the infection. For environmental application of immunoassay, detection of antigens is required since these are the toxic agents that disable personnel. As a result, environmental immunoassay biosensors require the development of antibodies to the biomaterials of interest before detection can be performed. This is in contrast to most biomedical applications, where a known antigen is often used to detect antibodies that are produced in the host's body in response to that same antigen, indicating the presence of the disease.

Nucleic acid probe hybridization (binding) provides a convenient way of detecting and measuring specifically defined nucleotide sequences in target analytes. By immobilizing a particular gene probe sequence, homologous gene sequences in target analytes bind specifically to the immobilized probe allowing direct detection of the target analyte. Gene probes can be made of either DNA or RNA and typically contain anywhere from 25 bases (nucleotides) to 10 kilobases. The target analyte can be upwards of a million bases in size. Since genetic information is highly specific, nucleic probes promise high sensitivity and specificity.

Heretofore surface plasmon resonance sensors were known. A conventional surface plasmon resonance sensor is typically based on a free space configured prism. For example, U.S. Pat. No. 4,844,613, the entire contents of which are hereby expressly incorporated herein, discloses an optical surface plasmon sensor device that uses a free space configured prism. U.S. Pat. No. 4,997,278, the entire contents of which are hereby expressly incorporated herein, discloses biological sensors based on surface plasmon resonance using a free space configured hemispheric prism. U.S. Pat. No. 5,064,619, the entire contents of which are hereby expressly incorporated herein, discloses biological sensors based on surface plasmon resonance using free space configured movable reflectors and a separate sensing surface chip that is index matched to a free space configured prism. Similarly, U.S. Pat. No. 5,055,265, the entire contents of which are hereby expressly incorporated herein, also discloses biological sensors based on surface plasmon resonance using free space configured movable reflectors. World Intellectual Property Organization International Publication Number WO 90/05305, the entire contents of which are hereby expressly incorporated herein, discloses a biosensor system based on surface plasmon resonance using a separate sensing surface chip that is index matched to a free space configured prism.

Surface plasmon biosensors are basically sensitive refractometers that monitor changes in the optical state of immunochemical or nucleic acid probe layers. This is accomplished by depositing a biosensing layer on top of a thin metal film evaporated onto the base of a TIR prism as shown in FIG. 3(a), which depicts an SPR immunoassay biosensor configuration. The SPR occurs at a specific angle of incidence that depends on the optical properties of the metal film, 10, and biosensing material, 40, coated on the metal film, 10. When TM-polarized light in the prism, 30, is incident at the proper angle to excite surface plasmons, the TM-polarized light is attenuated drastically. In the presence of a target bioagent, 50, the thickness and refractive index of the effective "dielectric" layer changes, thereby altering the angular position of the SPR as shown in FIG. 3(b). By measuring the shift in the plasmon resonance angle as a function of time ($\Delta\theta/\Delta t$), the concentration of bioagent can be quantified.

A previously recognized problem concerning surface plasmon sensors has been that in order to sense the attenuated region, the angle of reflectance must be located accurately so as to be detected by photosensors. A previously recognized solution was to rotate either the light source or the prism so that the attenuated region would be incident upon a detector array. A drawback of this previously recognized solution is that complex optical and mechanical systems were required. Moreover, during the rotation, more binding of the analyte will occur, thereby altering the position of the attenuated region. To date, the only commercial SPR based biosensing system is an extremely bulky device that requires replacing two components each time a measurement is made and is totally unsuitable for use as a compact, handheld sensor system.

SUMMARY OF THE INVENTION

The present invention is directed to a surface plasmon resonance sensor comprising a planar waveguide cartridge comprising: a planar waveguide; and a metal film connected to the planar waveguide; a sample flow cell adjacent the planar waveguide cartridge; a transverse magnetic polarized light source optically connected to the planar waveguide; a cylindrical diverging lens optically connected to the planar waveguide; and a detector array comprising a plurality of photodetectors optically connected to the cylindrical diverging lens.

This document discusses direct and indirect waveguide approaches to surface plasmon resonance sensing. Key preferred components are passive SPR resonance profiling using beam shaping optics and CCD detectors, a replaceable, multibounce waveguide sensor cartridge with specially angled input and exit faces, and diverse surface coated chemistries including immunoassays and nucleic acid probes. The biosensor promises to be very compact in comparison to existing SPR technologies and could be provided as a handheld device.

A principle object of the present invention is to obviate the need for index matching of biosensor substrates to TIR prisms by providing a multiple-bounce substrate-mode metal film coated waveguide cartridge with the recognition biochemistries deposited directly on the surface of the metal film.

Another object of the present invention is to lower the optical alignment tolerances and obviate the need for dynamic optic components by providing the reflector surfaces within the waveguide and the plasmon resonance interface directly on the waveguide.

Another object of the invention is to improve sampling efficiency by providing multiple biochemical sensing and reference channels in the same waveguide cartridge.

It is still another object of the present invention to provide a self-referencing design to quantify non-specific binding.

A further object of the invention is to achieve a high level of miniaturization by providing an apparatus having low bulk and a compact physical profile.

Other objects, advantages and features of the present invention will be more readily appreciated and understood when considered in conjunction with the following detailed description and drawings.

BRIEF DESCRIPTION OF THE DRAWINGS

These and other aspects of the invention are apparent from the purely exemplary, and therefore not restrictive, embodiments illustrated in the following drawings, in which:

FIG. 1 (a) illustrates surface plasmons at the interface between a metal and a dielectric;

DESCRIPTION OF THE PREFERRED EMBODIMENTS

Figures 1A, 1B:
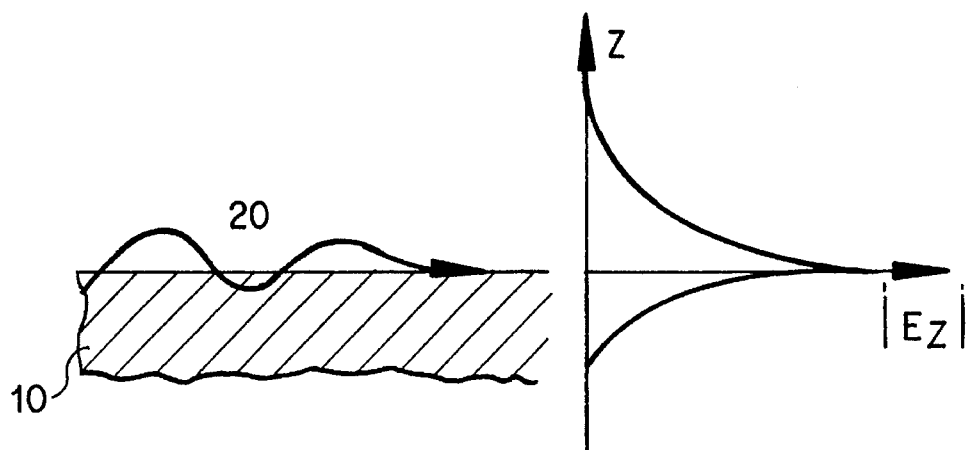
FIG. 1(b) illustrates the magnitude of the electric field of the charge fluctuations shown in FIG. 1(a)
Figure 2A:
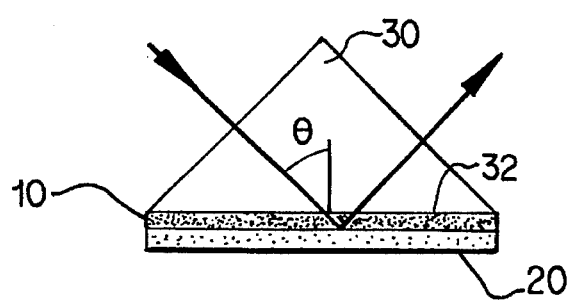
FIG. 2(a) illustrates surface plasmon resonance through prism coupling.
Figure 2B:
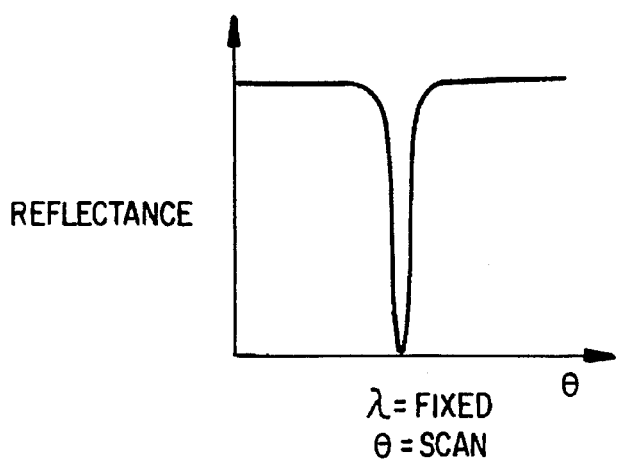
FIG. 2(b) illustrates reflectance near plasmon excitation.
Figure 3A:
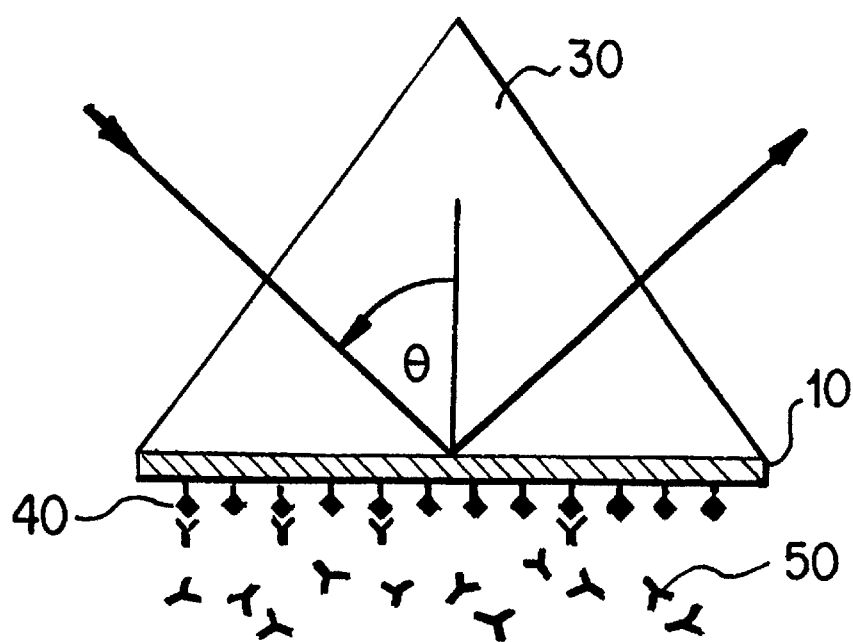
FIG. 3(a) illustrates depicts an SPR immunoassay biosensor configuration.
Figure 3B:
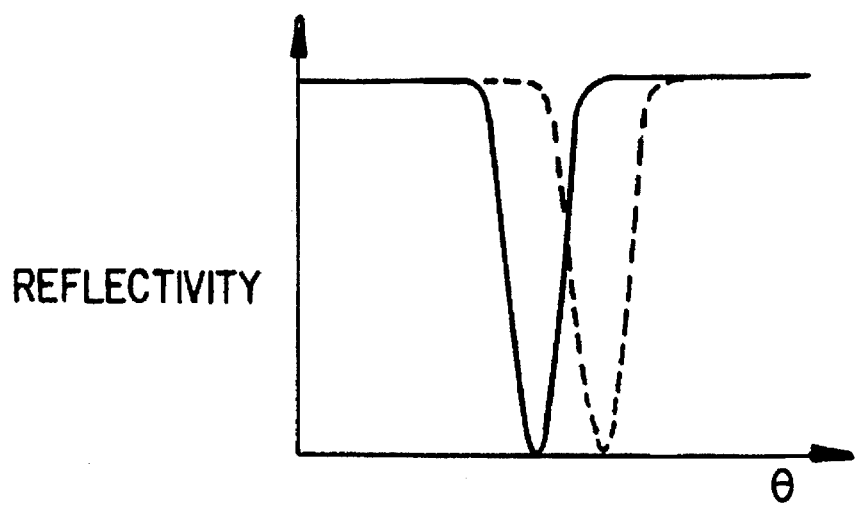
FIG. 3(b) illustrates an altered angular position of SPR.

All the disclosed embodiments can be made using conventional components, compounds and procedures without undue experimentation. All the disclosed embodiments are useful.

The invention and various advantageous details thereof are explained more fully below with reference to exemplary embodiments and with the aid of the drawings. In each of the drawings, parts the same as, or equivalent to each other, are referenced correspondingly.

Waveguide surface plasmon resonance sensor designs permit significant miniaturization of SPR sensing. Two different sensing methods are possible with very similar surface plasmon resonance system designs. The first design is a "direct" sensor where shifts in the surface plasmon resonance of a biochemical recognition layer are measured directly as a function of the binding of target analytes to the recognition layer. The second design is an "indirect" sensor where the excitation of surface plasmon resonances is used to enhance the signal of "indirect" fluorescent labels, which bind to target analytes bound to the recognition layer. Recognition layer biochemistries can include immunoassays and nucleic acid probes.

The present invention can include the following advantageous features. The present invention can include a special multiple-bounce (1 to n), substrate-mode waveguide cartridge with recognition chemistries deposited on its surface. An advantage of this design is that index matching of sensor substrate to a separate prism is not required. The present invention can include chemical sensing and reference channels deposited on the same metal film coated waveguide cartridge. The present invention can include angle polished waveguide endfaces to couple laser light to angles that excite surface plasmon resonances in the recognition layers. An alternate approach would be to use grating couplers appropriately located on the surface of the waveguide cartridge structure. The present invention can include laser light that is focused by lenses into the waveguide cartridge such that the surface plasmon resonance angles are passively probed by the laser light. Lenses may or may not be advantageous to further shape the light that exits the waveguide cartridge before detection depending on the particular system configuration. The present invention can include passive detection of "direct" recognition layer response through the use of (n ×n) detector arrays such as linear reticon devices or CCD detectors, which monitor the intensity of all ray angles guided in the waveguide cartridge. The present invention can include passive detection of "indirect" recognition layer response using either discrete photodetectors or detector arrays to detect fluorescent emission of labeled chemistries on the surface of the waveguide cartridge.

DIRECT SENSOR

In a preferred embodiment of a "direct" biosensor version of the present invention, light from a collimated laser diode module is TM-polarized and focused (converged with a convex cylindrical lens) into a waveguide sensor element. The guided light couples and generates surface plasmon resonance (SPR) in a metal film/immunoassay biolayer deposited directly on top of the waveguide. A concave cylindrical lens diverges the light exiting the waveguide onto an enclosed CCD array, enhancing the sensitivity of the device. A particularly preferred embodiment is a handheld SPR biosensor having a replaceable waveguide sensor element cartridge.

The two different SPR "direct" biosensor systems have similar optical designs. The closely related systems are single-channel and multi-channel devices read by linear and two-dimensional detector arrays, respectively. Each of the systems uses a specially designed waveguide biosensor wherein changes in the permittivity and thickness of a biosensing layer are used to modulate the surface plasmon resonance.

Figure 4A:
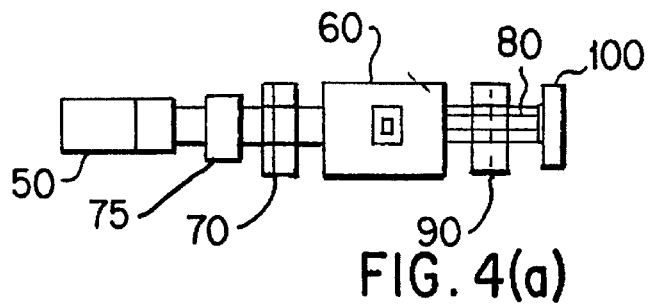
FIG. 4(a) illustrates a top view of a single-channel biosensor system according to the present invention.
Figure 4B:
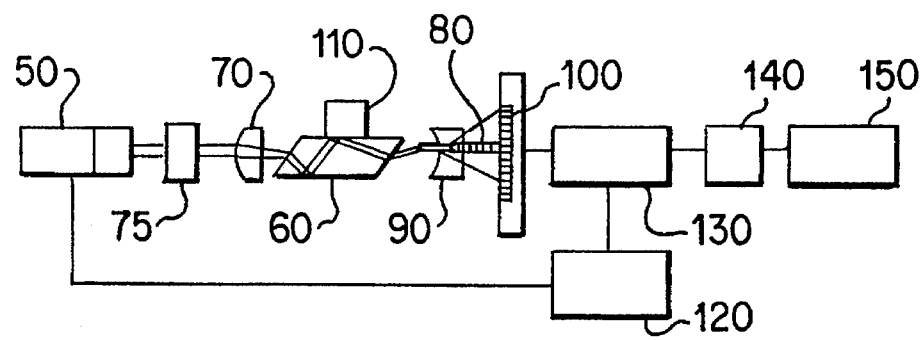
FIG. 4(b) illustrates a side view of a single-channel biosensor system shown in FIG. 4(a)

FIGS. 4(a) and 4(b) illustrate the design concept for the single-channel research biosensor system. FIG. 4(a) is a top view and FIG. 4(b) is a side view. In the design, TM-polarized light from a collimated laser diode, 50, is focused into a specially coated substrate-mode waveguide, 60, by a convex cylindrical lens, 70, after passing through a polarizer, 75. Referring to FIG. 4(b), in this embodiment, the waveguide, 60, is a two bounce waveguide. The convex cylindrical lens, 70, is a focusing lens that enables the system to be passive, with no moving parts, by converging the light and producing an angular bandwidth of light in the waveguide. The light interacts with the biosensor coating, which attenuates the rays incident at angles that couple into the surface plasmon resonance, resulting in a dark band, 80, in the output light, as seen in FIG. 4(b). A concave cylindrical lens, 90, is a cylindrical diverging lens that expands the beam onto the linear CCD Reticon array, 100, which monitors the intensity of the transmitted rays and detects translations of the position of the absorbed light in the presence of analytes as a shift in the band location on the detector array. A special sample injection flow cell, 110, is a fitting that is used to inject activating buffers onto the biosensor coating on the waveguide and/or to inject samples for screening. A DC power supply, 120, powers the system. Signal from the array, 110, travel to the detection electronics, 130, then to an analog-digital interface, 140, and then to a processor and readout, 150.

Figure 5A:
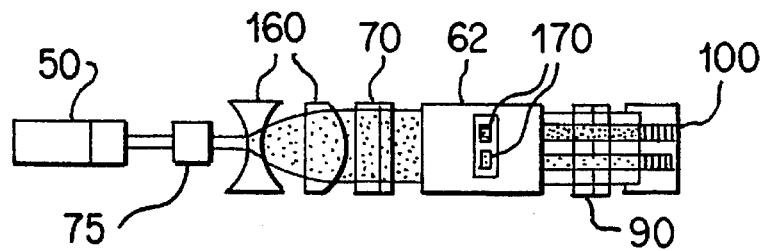
FIG. 5(a) illustrates a top view of an in-line dual-channel SPR biosensor according to the present invention.
Figure 5B:
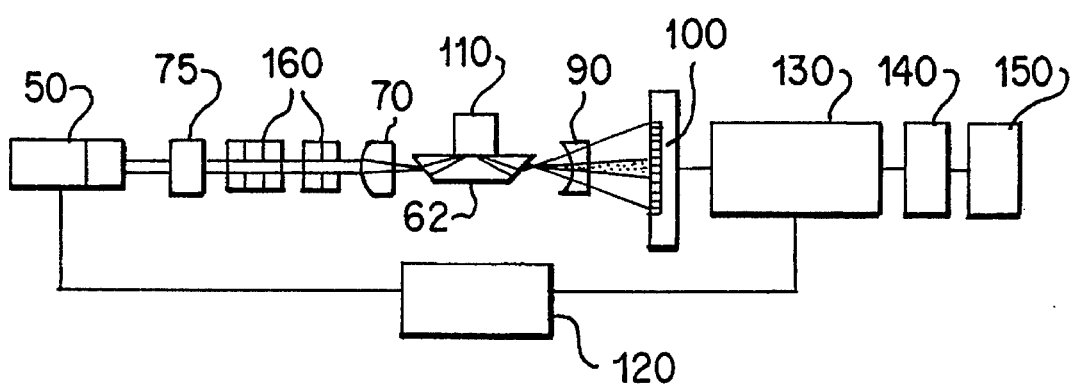
FIG. 5(b) illustrates a side view of the in-line dual-channel SPR biosensor shown in FIG. 5(a)
Figure 6A:
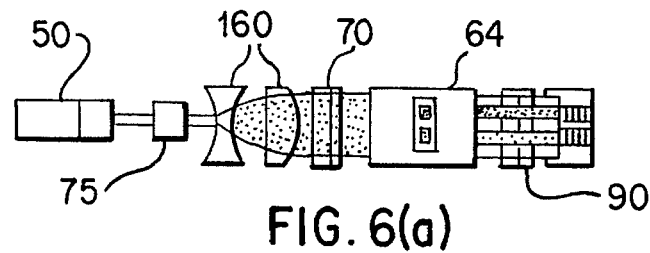
FIG. 6(a) illustrates a top view of a low profile in-line dual-channel SPR biosensor according to the present invention.
Figure 6B:
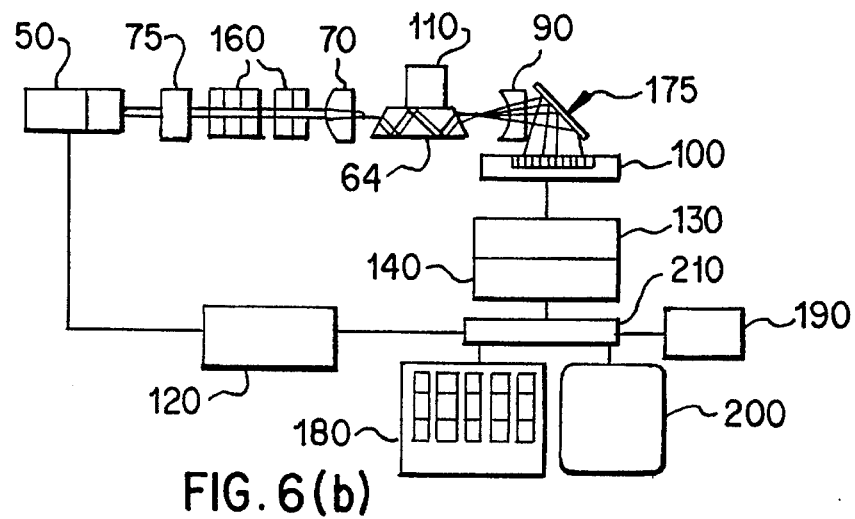
FIG. 6(b) illustrates a side view of the low profile in-line dual-channel SPR biosensor shown in FIG. 6(a)

FIGS. 5(a) and 5(b) and FIG. 6(a) and 6(b) present two different design concepts for a multiple-channel biosensor system. FIGS. 5(a) and 6(b) are top views while FIGS. 5(b) and 6(b) are side views. FIGS. 5(a) and 5(b) illustrate an in-line dual-channel SPR biosensor design concept. FIGS.

6(a) and 6(b) illustrate an in-line dual-channel SPR biosensor design concept. Comparison with FIGS. 4(a) and 4(b) reveals that the operating principle of the dual-channel system is the same as the single-channel system, except that a few extra components to accommodate the multiple-channel waveguide biosensor. Depending on the position and dimensions of the reference and sensor channels, an anamorphic beam expander, 160, may be required so that the light from the single laser diode source will interact with all spatially resolved channels, 170, on the surface of the waveguide cartridge. However, it may be that the beam cross-section of the laser diode is sufficiently wide to forgo the anamorphic lens system if the two channels can be placed close enough together, as dictated by the dual linear CCD Reticon array dimensions. The multiple channels of the waveguide biosensor are read out independently by the two dimensional detector array. Referring to FIG. 5(b), in this embodiment, the waveguide, 62, is a one bounce waveguide.

Referring to FIG. 6(b), in this embodiment, the waveguide, 64, is a three bounce waveguide. It should be noted that the structure of a waveguide providing more than three bounces will be the same as any of the structures used for one to three bounces depending on the number of bounces. FIG. 6(b) also depicts a mirror, 175, which results in an apparatus having a lower profile. The embodiment of FIG. 6(b) is shown with a keyboard, 180, an RS-232 link, 190, a liquid crystal display 200, and a microprocessor, 210.

Figure 7:
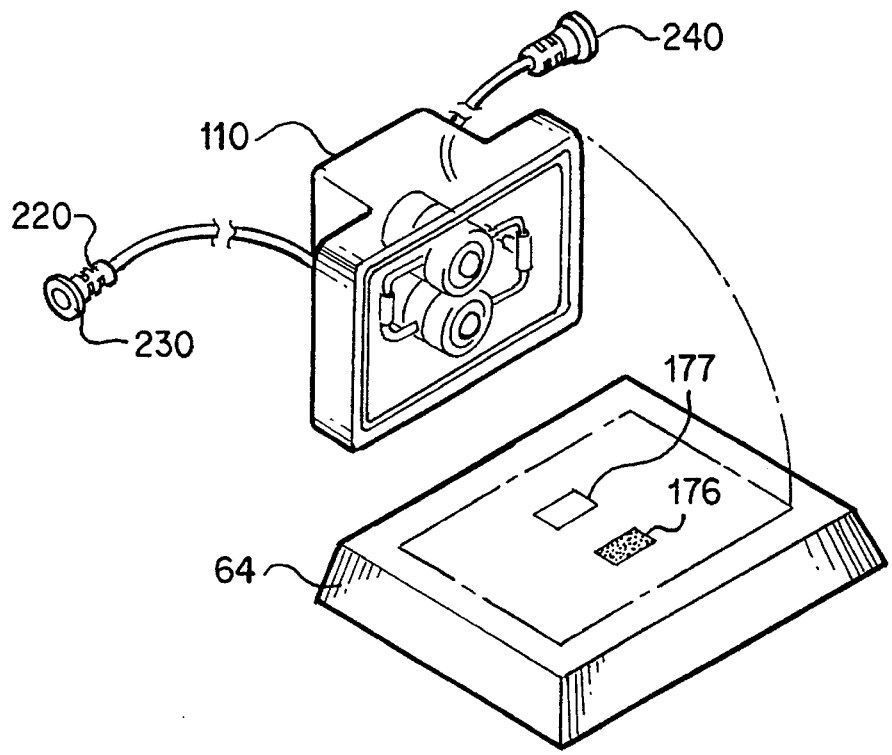
FIG. 7 illustrates a perspective view of a sample flow cell according to the present invention.

Referring to FIG. 7, the sample flow cell, 110, can be a multiple-channel injection hardware can introduce analyte to the reference channel, 176, and sensor channel, 177, simultaneously. The injection hardware includes an injection fitting, 220, a Luer lock 230, and an outflow fitting, 240. The injection hardware depicted in FIG. 7, is also useful in conjunction with multi-channel "indirect" sensors.

Electronics for the readout of the single or the multiple channel biosensor versions are interchangeable. Custom power-efficient CCD detector electronics and A/D conversion electronics can be read from the CCD array. An on-board microprocessor programmed by ROM can initiate data acquisition and store the results in RAM. The on-board microprocessor can also be responsible for data analysis and can be programmed appropriately for signal processing. An RS-232 link can allow the unit to communicate with a PC both for programming the microprocessor and for logging data from a handheld embodiment of the present invention.

In a preferred embodiment of the present invention, in order to log data associated with the surface plasmon resonance modulation, software routines were written to control a Keithley Metrabyte DAS-16 A/D card in a 486 PC. The A/D card monitors three signals generated by the CCD electronics. Signal A is a 5 volt start pulse generated by the pulse generator at the beginning of a sweep of the detector array pixels. It signals the A/D card to prepare to log data. Signal B is a 5 volt trigger pulse that is used to externally clock the A/D card to log data from Signal C. Signal C is a 0 to 5 volt analog data video signal generated from the linear detector array. After the start pulse is generated, when Signal B goes from low to high, the A/D card samples Signal C. Since the rising edge of Signal B is 90° out of phase with Signal C, the A/D card always samples the video state during the middle of its output. The A/D card is configured to read the data in "background" directly to RAM and, after the sweep is complete, transfer the data into an array in the "foreground." This insures that the data acquisition can be fast enough to log all 256 detectors in a single sweep. After the data is transferred to an array, it is written to a file for later analysis.

In a preferred embodiment, a software routine written in Quick Basic 4.5 was used to interface the CCD electronics with the A/D card and to write the data into a file for analysis. When the software is initiated, the user is provided with a menu that allows the user to modify the acquisition rate and duration, store the data to a file, and display the acquired data on the computer CRT. Six menu selections available to the user are: (1) "Start," begins the data acquisition. The software monitors the A/D card for start and trigger signals and collects the specified amount of data into a data file. (2) "Change File Name," allows the user to change the name of the file in which the data is stored before each data acquisition is initiated; (3) "Change Delay Count," is used to specify the number of start pulses to be detected before each data acquisition begins. Since start pulses are separated by 100 ms, this menu option is actually used to specify the length of time between each data cycle. (4) "Change Number of Cycles," is used to specify the number of data acquisitions that can be written to the data file. (5) "Display Data," plots the data directly onto the computer screen so the plasmon resonance shift can be seen in quasi-real time; (6) "End," shuts down the program.

In a preferred embodiment, the electronic system includes a Hamamatsu C4069 CCD detector array, a Hamamatsu C4091 pulse generator, a Hewlett Packard DC power supply, a Keithley Metrabyte 12 bit A/D card, and a Lecroy digital oscilloscope. Electrical power for the CCD detector array, the pulse generator, and the laser diode used for monitoring the plasmon resonance is provided by the DC power supply. The start pulse, provided by the pulse generator, is wired into the A/D card and oscilloscope with standard coaxial components. The oscilloscope is wired in parallel with the A/D card and is not necessary for actual data acquisition. It does provide a real-time display of the surface plasmon resonance shift and is useful to insure that the system is operating properly. The trigger pulse, which is used as an external clock for data acquisition, is also wired into the A/D card. Data is provided to the A/D card and oscilloscope for display from the video output in the form of a 0–5 V analog signal.

A single channel embodiment can use a vertical detector array. The alternate design, shown in FIGS. 6(a) and 6(b) as dual-channel embodiment, can result in a much lower profile for the optical train by using a 45° mirror to reflect light from the waveguide onto a horizontally mounted two dimensional detector array.

Figure 8A:
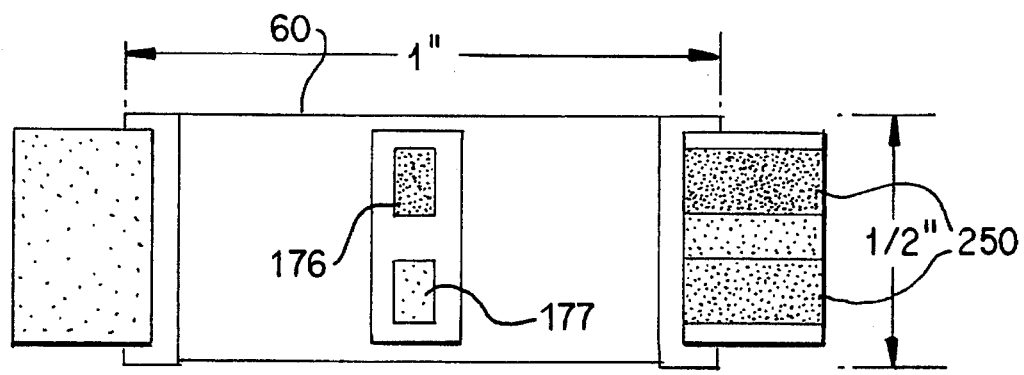
FIG. 8(a) illustrates a top view of a substrate mode waveguide to be used in a biosensor system according to the present invention.
Figure 8B:
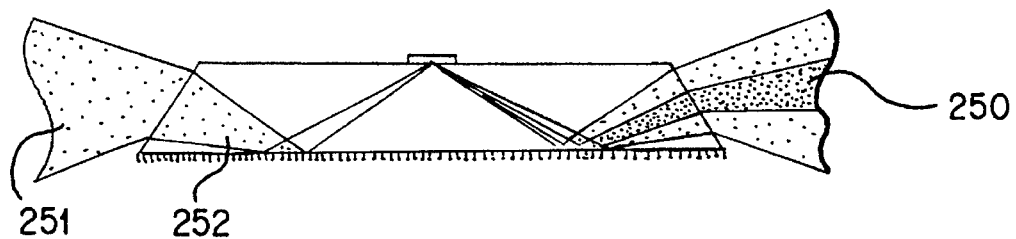
FIG. 8(b) illustrates a side view of the substrate mode waveguide shown in FIG. 8(a)

FIGS. 8(a) and 8(b) illustrate a substrate mode waveguide, 60, to be used in the biosensor system. As shown in FIG. 8(a) the darker shaded area toward the top of the drawing represents the reference channel, 177, while the lighter shaded area toward the bottom of the drawing represents the sensor channel 176, having a biolayer sensing element. Multiple sensor channels (up to n) are possible, though only one sensor channel, 176, and one reference channel, 177, are shown in FIG. 8(a). The waveguide substrate, 60, is approximately 1–2 mm thick and resembles a common microscope slide. Specially angled end faces can be polished so that an expanded laser beam focused into the waveguide contains ray angles that overlap the surface plasmon resonance angles of both the reference and sensing biolayers deposited on it. By insuring the angular bandwidth of the coupled light is around 10° inside the waveguide, the SPR resonance position can be measured passively without any mechanical angular adjustments.

The dark bands, 250, shown toward the right side of FIGS. 8(a) and 8(b) correspond to those rays that couple to the surface plasmon resonance and are thus attenuated. The focused beam, 251, is refracted, 252, when it enters the waveguide, 60. The position of the attenuated band is monitored by a CCD array. As the surface plasmon resonance position shifts, the dark band sweeps across the CCD array in proportion to the concentration of target analyte that binds to the recognition layer.

Figure 9:
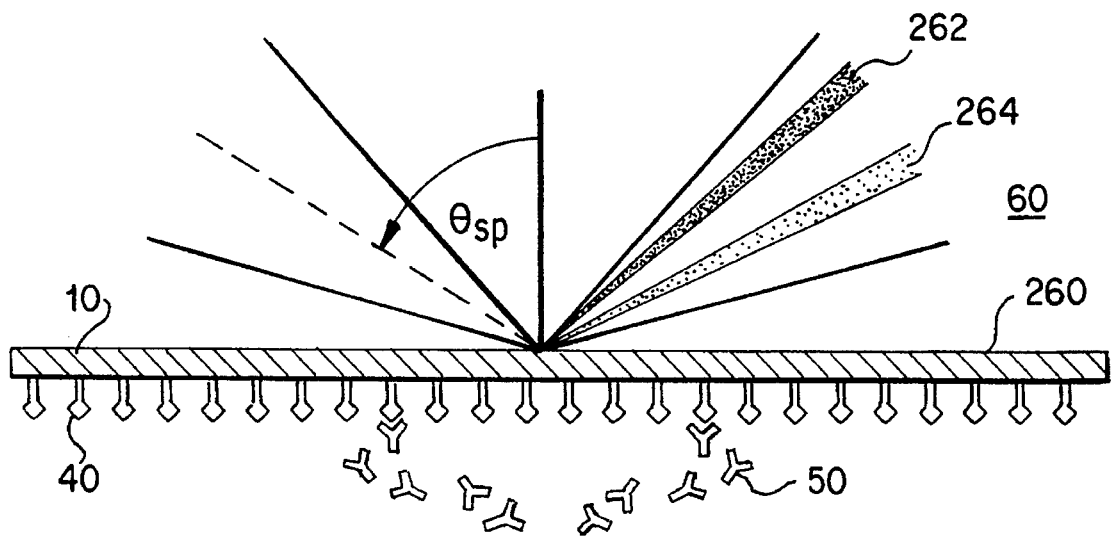
FIG. 9 illustrates light focused onto an interaction surface with ray angles spanning the SPR according to the present invention.

FIG. 9 illustrates light focused onto the interaction surface, 260, with ray angles spanning the surface plasmon resonance. The darker shaded area closer to the normal to the plane of the waveguide, 262, represents those rays that couple to the surface plasmon resonance and are thus attenuated when there are no bound antibodies. In contrast the darker shaded area further from the normal to the plane of the waveguide, 264, represents those rays that couple to the surface plasmon resonance and are thus attenuated when there are bound antibodies.

Figure 10:
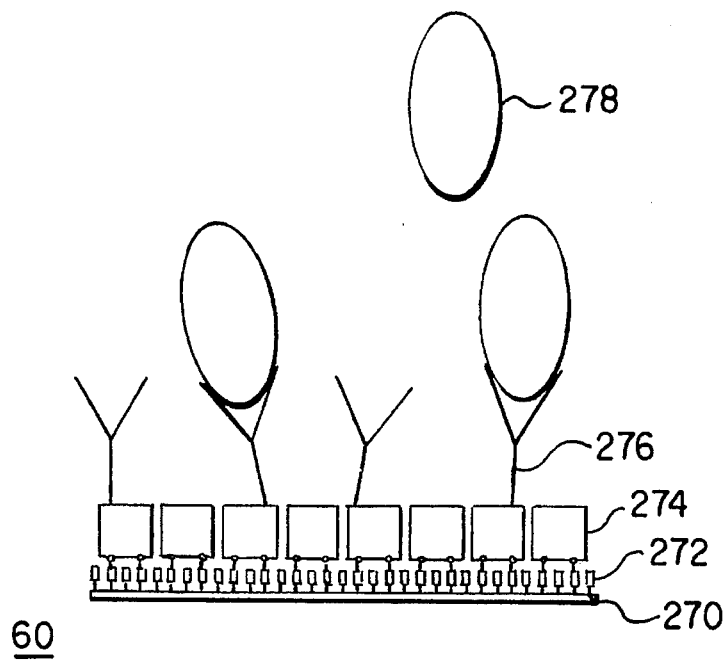
FIG. 10 illustrates a view of a steptavidin/biotin thin film multilayer used to form an SPR immunosensor according to the present invention.

FIG. 10 diagrams the way that a streptavidin/biotin thin film multilayer can be used to form an SPR immunosensor. A thin film of gold, 270, is evaporated on a waveguide substrate, 60, and onto the film is immobilized a layer of biotin, 272. A monolayer of streptavidin, 274, is then immobilized to the biotinylated gold surface. Streptavidin is a tetravalent protein obtained from *Streptomyces avidinii* which possesses four biotin binding sites arranged in pairs on opposite faces of the molecule. Once the streptavidin film binds to the biotinylated gold surface, it can be used as a linking molecule to bind the sensing biochemistry. See references (19, 20). In FIG. 10, a biotinylated antibody, 276, is shown bound to the streptavidin, 274. The biotinylated antibody binds to the antigent to be detected, 278.

One of the major considerations in the final selection of an immobilization chemistry will be its non-specific binding activity. For a direct biosensor, minimizing non-specific binding will enable more sensitive measurements.

Recently, a superior covalent binding method has been described in U.S. Pat. No. 5,077,210, the entire contents of which are hereby expressly incorporated by reference. The method provides high surface density of protein attached to the surface while maintaining high binding specificity. It uses a thiol-terminal silane, mercaptopropyl trimethoxysilane (MTS) for coating of the fiber surface, and a heterobifunctional crosslinker, N-gamma-maleimidobutyryloxy succinimide ester (GMBS), for protein attachment. GMBS reacts at one end with thiol groups of the silane coating, and at the other end with terminal amino groups of the antibody. With this method, antibodies can be immobilized at high density (el.g., 2 ng/mm$^2$). The relative amounts of antigen bound by the immobilized antibody can be 3 to 4 times higher than those obtained with some other antibody-immobilization methods. The amount of nonspecific binding can be reduced to 2 to 5% of the total binding by addition of blocking agents (BSA, ovalbumin, sugars, dextran, etc.). With this low background, antigen binding can be measured at levels as low as 150 femtomoles when an antigen concentration of 3 picomoles/ml is applied. Antibodies immobilized by this method can maintain their bioactivity for over 18 months. Though this technique has been successfully demonstrated for immunoassay biosensors, its suitability for nucleic acid probe immobilization is yet to be determined and modified crosslinking chemistries may likely have to be developed in any case.

In order to utilize this technology, a thin (e.g., <50 Å) layer of $SiO_2$ can be deposited on the metal film that coats the waveguide substrate. Since the sensing evanescent field of the surface plasmon resonance extends roughly 1 μm above the metal film, this probably will not adversely affect sensitivity. In fact, if the $SiO_2$ layer sufficiently passivates the metal film surface, silver films could be more advantageously be used. Silver films typically produce more sensitive SPR biosensors than chemically inert gold films.

A third type of surface immobilization technique uses polymer hydrogel matrices. These materials typically contain a large amount of water, are soft, and bioinert. Examples include cross-linked polymer films of poly(vinyl alcohol), reference (21), and films of carboxymethyldextran, references (22–23). In the latter technique a monolayer of long chain 1,w-hydroxyalkyl thiols forms a hydrophilic surface on the gold. This metal protection layer serves partly to prevent proteins from contacting the metal surface, and partly to facilitate carboxymethyldextran binding. The carboxyl-modified hydrogel is deposited by a series of steps that results in a negatively charged matrix that can be covalently bound to a variety of ligands. Once the hydrogel matrix is deposited on the waveguide, either antibodies, antigens, or nucleic acid probes can be immobilized on the surface provided they can be cross-linked with suitable ligands.

Depending on the immunoassay or nucleic acid probe chemistry selected, the hydrogel technique may offer one of the best solutions. The hydrogel technique's covalent binding properties may be more generic and thus more widely applicable than the silanization technique. Also, hydrogel matrices demonstrate much higher protein immobilization densities, which promises the potential of greater biosensor sensitivity and less non-specific binding.

Figure 11:
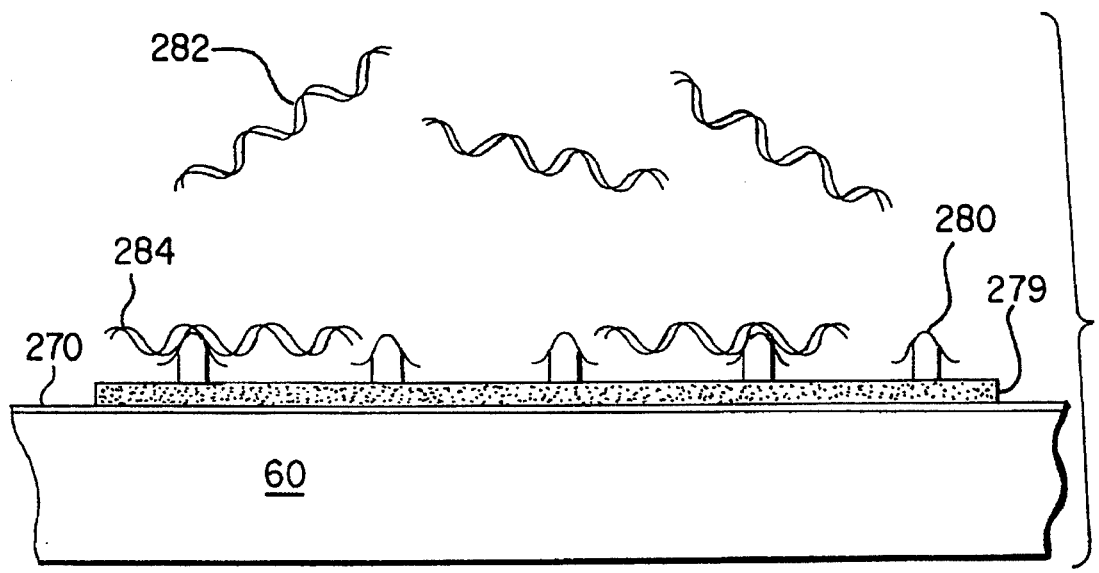
FIG. 11 illustrates a biosensor according to the present invention incorporating a probe sequence corresponding to a portion of a conserved gene of the HIV genome.

FIG. 11 is a diagram of a biosensor incorporating a probe sequence corresponding to a portion of a conserved gene of the HIV genome, 282, such as the region of the gag gene commonly used in polymerase chain reaction detection procedures. See reference (8). A gold metal film, 270, can be deposited on the waveguide substrate to an appropriate predetermined thickness using SPR modeling software. On the metal film, 270, a nucleic acid probe, 280, can be immobilized in a fashion very similar to techniques used for surface-immobilized sandwich hybridization, e.g. by coating the metal film with streptavidin and reacting with a biotin-linked probe, 279. The secondary labeling of the target DNA or RNA (which creates the sandwich) is not necessary, since the binding of the target genes to the conjugate receptors, 284, can be monitored directly by surface plasmon resonance. Reference (9) discusses issues associated with prism-based SPR DNA probe sensing.

Nucleic acid probe hybridization (binding) provides a convenient way of detecting and measuring specifically defined nucleotide sequences in target analytes. By immobilizing a particular gene probe sequence, homologous gene sequences in target analytes bind specifically to the immobilized probe allowing direct detection of the target analyte. Gene probes can be made of either DNA or RNA and typically contain anywhere from 25 bases (nucleotides) to 10 kilobases. The target analyte can be upwards of a million bases in size. Since genetic information is highly specific, nucleic probes promise high sensitivity and specificity.

Figure 12:
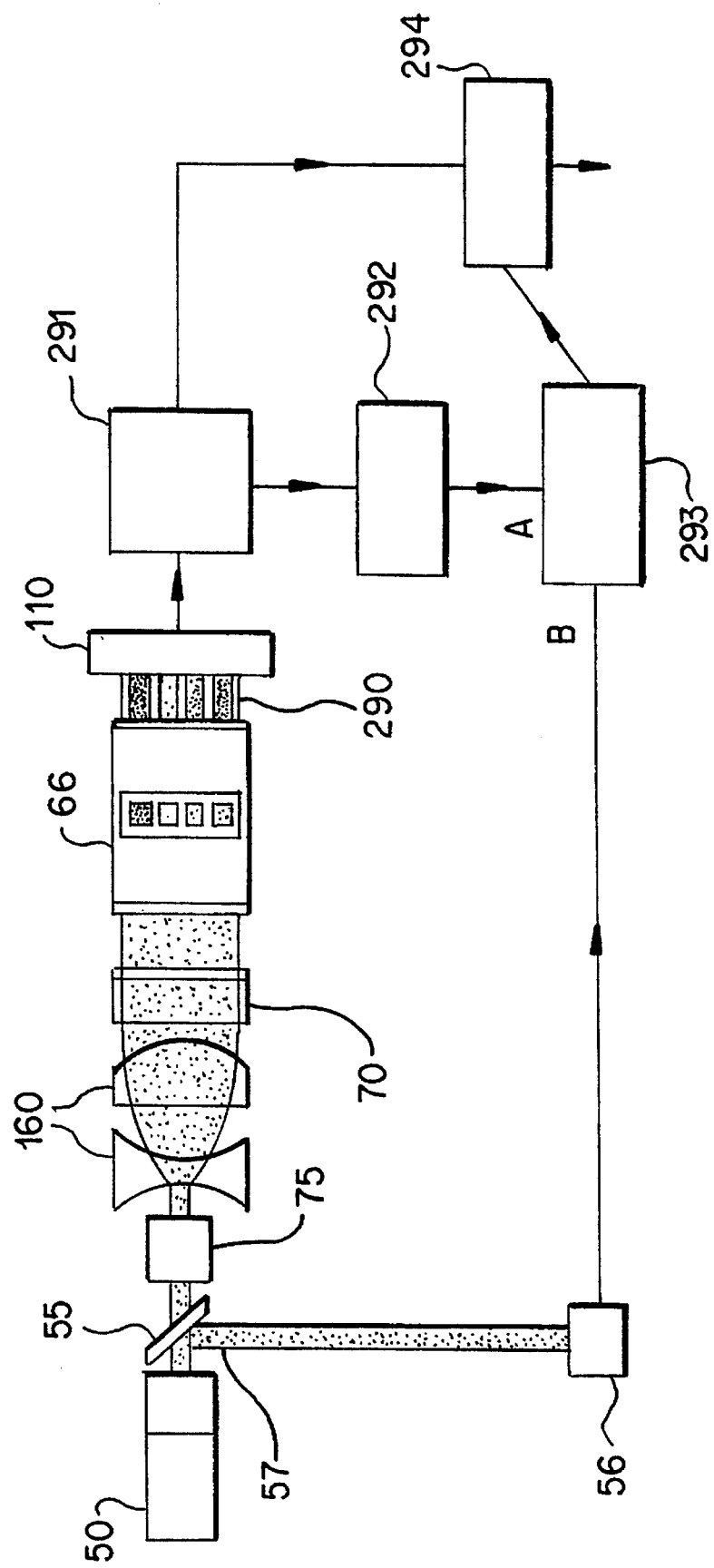
FIG. 12 illustrates a top view of a multi-channel SPR nucleic acid probe waveguide biosensor system according to the present invention.

FIG. 12 illustrates a preferred optical design for a multichannel SPR nucleic acid probe waveguide biosensor system. This compact optical system can be used to monitor the waveguide biosensor discussed in the previous section. Light from a collimated laser diode, 50, passes through a beamsplitter, 55, a polarizer, and a series of lenses before coupling to the multi-channel waveguide, 66. The light, 57, from the beamsplitter, 55, is coupled to a reference photodiode, 56, which monitors source stability and thermal drift.

The anamorphic beam expander, 116, is a lens system that expands the collimated laser beam in only one direction (i.e., in the plane of the page). By so doing, the same laser source can simultaneously monitor all channels of the sensor. A cylindrical lens, 70, focuses the beam into the waveguide sensor to produce an internal 10° cone of light centered about the unmodulated surface plasmon resonance angle of the sensor, as discussed in the next section. The SPR modulated light exiting the sensor, 290, is monitored with a two-dimensional CCD array, 110. Each sensing channel can be associated with a column of pixels, several pixels wide, on the 2-D CCD array, 110. Slight lateral shifts that would destroy alignment in channel-waveguide systems only cause the array of columns to shift a few pixels to the left or right. Simple pattern recognition software can easily associate each column on the CCD array, 110, with its proper sensor "channel" on the waveguide. A driver/amplifier board, 291, sweeps the array and puts out an analog video signal and timing pulses. A scaling amplifier, 292, adjusts the analog video amplitude for ratioing with the reference photodiode signal at a ratio mixer, 293. For example, a CCD pixel with a ratioed output of 1.0 would be monitoring guided rays that did not couple to surface plasmon modes at all. The output of the CCD array can be stored in a personal computer using an A/D card, 294. A possible option is to use a CCD camera and a frame grabber to input the video signal. However, this would require post-processing to give a ratiometric output.

A benefit of the device depicted in FIG. 12 is that it allows multiple sensor channels to be multiplexed on a single waveguide without the optical alignment tolerances required for integrated optic waveguide and fiber optic sensors. The relatively thick waveguide (~2 mm) insures complete coupling of light for unskilled and skilled operators alike. The simultaneous real-time monitoring of the reference and sensor channels compensates for any variations in alignment.

Referring again to FIGS. 8(*a*) and 8(*b*), because the guided beam senses both the reference channel, 176, and the sensor channel, 177, simultaneously with rays of equivalent angles, the actual resonance shift can be measured relative to the reference channel. The reference channel, 176, incorporates a deactivated sensing layer, yet is still sensitive to the refractive index of the serum being sampled and to non-specific adsorption of proteins. Using processing algorithms, data on the shift measured from the reference channel and the sensing channel are combined to yield the shift produced by the target analyte alone. Because the shift is being measured with respect to the reference channel, 176, which is probed by rays of the same angle as the sensing channel, the optical alignment requirements of this sensor system are minimal. This is in contrast to prism-based and grating-based SPR sensors, whose accuracy requires precise angular control for accurate measurements. Also, because index matching between a separate sensor substrate and a prism is not required, the overall system design is much simpler and better suited to applications where a compact, rugged device is required.

This self referencing capability significantly increases the performance of the present SPR sensor over competing technologies by compensating for non-specific absorption which leads to misleading results and inhibits the realization of SPRs sensitivity. For example, Pharmacia's BIACORE™ SPR system exhibits sensitivities of $10^{-9}$ mol/l for purified samples. However, when sensing directly from blood serum, sensitivities of only $10^{-6}$ mol/l can be achieved with reliability. This is presumed to be due to non-specific adsorption of proteins in the serum. By passively compensating for this type of interference, the present SPR sensor system is expected to exhibit significantly increased sensitivity and selectivity when compared to present SPR technologies.

Figure 13:
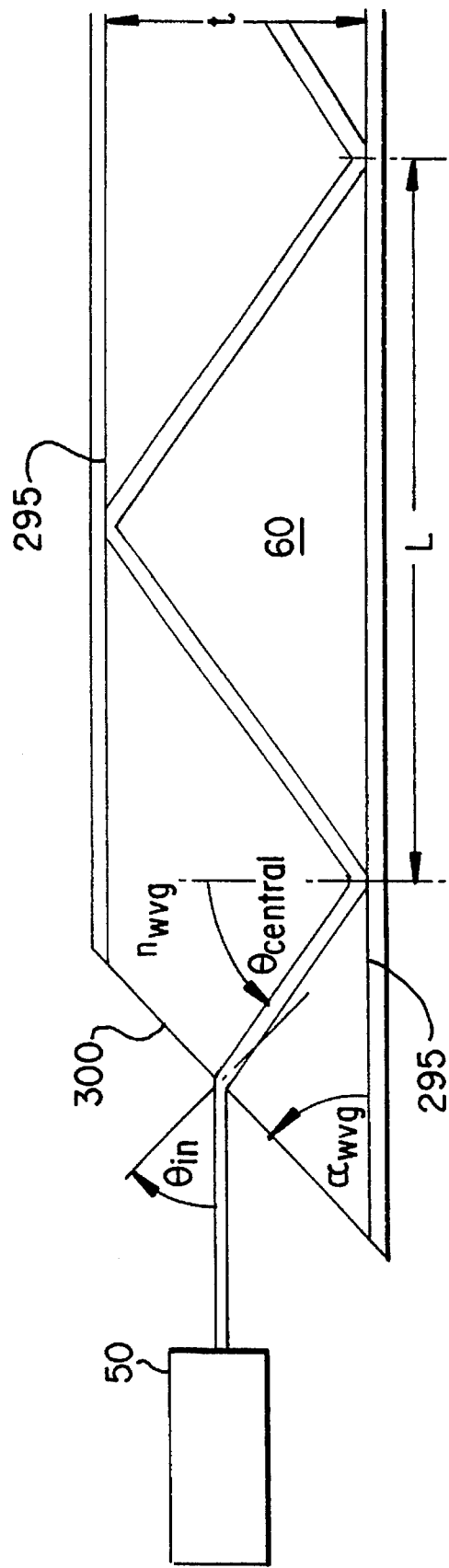
FIG. 13 illustrates a side view of the geometry of an angled waveguide input/output interface according to the present invention.

FIG. 13 illustrates the geometry of an angled waveguide input/output interface. The planar waveguide includes a plurality of reflector surfaces 295 within the planar waveguide. For a low profile biosensor, it is necessary for the axis of the laser light source (i.e., the collimated laser diode, 50) to be in the plane of the waveguide biosensor, 60. In order to achieve this design goal, the angled sensor face, 300, should be polished so that the laser diode light probes the surface plasmon resonance with sufficient angular bandwidth, $\Delta\theta_{total}$, centered about $\theta_{central}$ when the laser beam is focused through a series of cylindrical lenses. The basic condition arises from the constraint that the unfocused laser beam must directly couple to $\theta_{central}$ by refraction at the polished interface, as shown in FIG. 13.

From Snell's law and geometrical considerations, it follows that the tangent of the waveguide input angle must satisfy where $n_{wvg}$ is the refractive index of the waveguide cartridge.

$$\tan \alpha_{wvg} = \tan \theta_{central} - \frac{\sec \theta_{central}}{n_{wvg}} \quad (6)$$

By polishing a waveguide at $\alpha_{wvg}$, it follows that light focused into the waveguide around the collimated direction passively probes both sides of the resonance position. The result is that the substrate simultaneously guides light rays arriving at suitable angles to interact with surface plasmon resonances in biosensor films deposited on the surfaces. The input laser light will eventually focus at some point inside the waveguide cartridge after multiple bounces. At distances greater than the focal point, the light will begin to diverge. The system is designed so that the light focuses near the halfway point, or symmetry point, of the optical path of the rays traversing the waveguide, as seen in FIGS. 8(*a*) and (*b*). This helps to insure that the exit spot is similar in size to the input spot so that no information will be lost at the exit. For example, if the substrate were only 2 mm thick, and the exit spot had expanded to 3 mm, some of the rays would be scattered at the exit and would not be available for monitoring the SPR response.

INDIRECT SENSOR

In a preferred embodiment of an "indirect" biosensor version of the present invention, there are several additional considerations surrounding the application of a waveguide cartridge. If light is incident on a prism at an angle greater than the critical angle for total internal reflection (TIR), an evanescent wave is produced below the reflecting surface of the prism. The evanescent wave decays exponentially in the direction normal to the prism's surface. This same effect occurs in any optical structure where TIR guides the light, such as in planar waveguides and optical fibers. See references (10, 11). In evanescent field fluorescence biosensors, it is this evanescent field that is used to excite fluorescent labels immobilized with appropriate biochemistry on the sensing surface. The emitted fluorescence is then detected directly or coupled through the evanescent field back into the waveguide. In the latter case, much smaller signals are exhibited, but for certain applications this is desirable since detection electronics and sensor probes can be separated for remote sensing.

Because the majority of the light is totally reflected in these evanescent sensors, only a small portion of the incident power is in the evanescent field. Thus, the excitation of fluorescence in thin biolayers on the TIR surface is not very efficient. However, as mentioned, the fact that the field is localized in the active sensing layer insures that bulk fluorophores are not excited, which would result in overestimation of the amount of analyte present if direct excitation were used. The primary advantage of evanescent fluorescence biosensors is that they are highly specific, highly sensitive, and allow rapid screening. The present invention combines these evanescent fluorescence strengths while simultaneously overcoming the inefficiency of standard waveguide excitation techniques in order to develop a superior sensor.

In biosensors based on fluoroimmunoassays, for example, binding between antibody and antigen is registered by measuring the fluorescence intensity changes of a coated sensor after incubation with the corresponding fluorescent labeled immunological partner. Labeling is achieved by binding extrinsic fluorescent dyes to the antibody or antigen molecules. The dyes that are used most frequently in conventional fluorescence immunoassays (e.g., fluorescein isothiocyanate, tetramethyl rhodamine isothiocyanate, and Texas Red), are excited at wavelengths that are not presently available from high-power semiconductor sources and thus are not suitable for compact, portable biosensor systems.

An important class of dyes developed for use as fluorescent labels for immunochemicals and other biomolecules are the isothiocyanate derivatives of cyanine dyes. See references (12–14). These dyes have maximum absorbencies in the red and near infrared regions of the spectrum and have reasonably good fluorescence quantum yields and extinction coefficients. They also are relatively easy to attach to proteins, having protein reactivities very similar to fluorescein isothiocyanate. Several derivatives of these compounds exist, but the most interesting of these for our purposes is the class of 5-t-butyl carbamide derivatives. The compound named "CY7.8NHBOC" by its discoverers in Waggoner's group at Carnegie Mellon University, reference (12), has its maximum fluorescence excitation near a wavelength of 750 nm and thus it is well suited for use with common, inexpensive laser diode sources developed for the compact disk industry.

Standard evanescent fluorescence biosensors have very high specificity and sensitivities but suffer from very small signal levels, which require sensitive detection electronics. With the present development of infrared labels for biosensing, see reference (15), it is now possible to use semiconductor laser sources to excite these sensors. However, signal intensities are still small. Therefore, merging the technique of surface plasmon resonance with the technique of fluorescence becomes advantageous, since SPR can be used to increase the excitation intensity by over two orders of magnitude. See reference (16).

Figure 14:
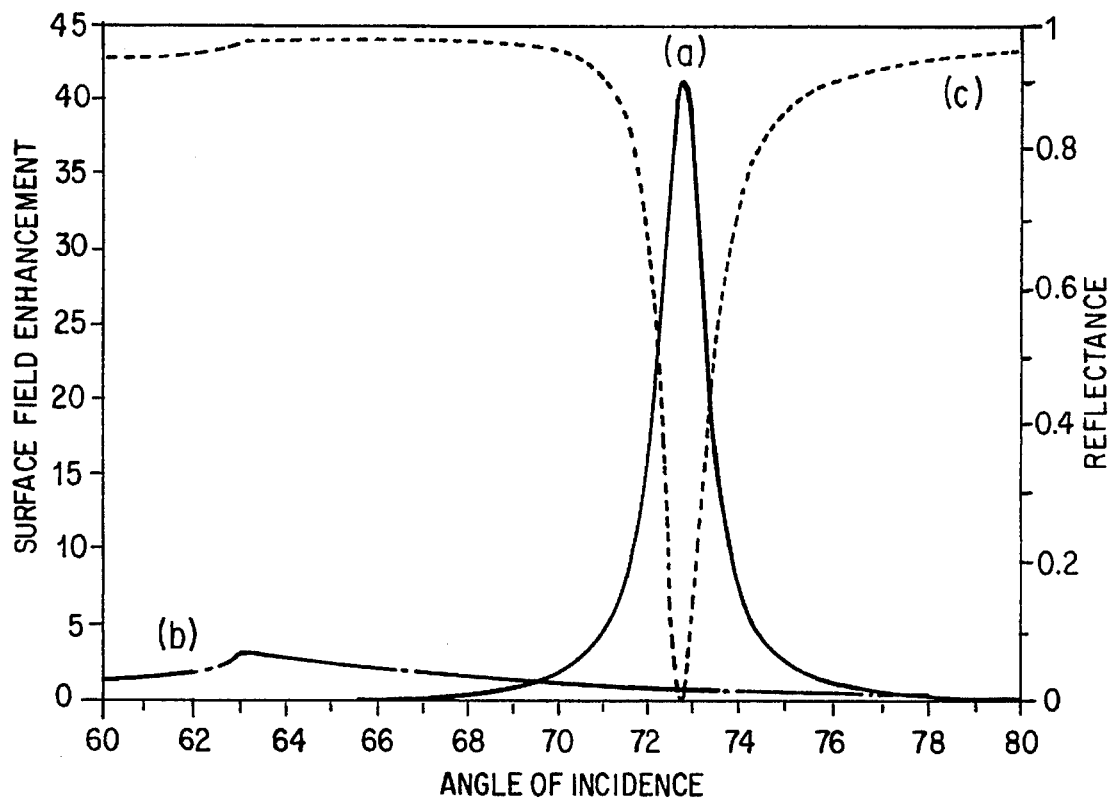
FIG. 14 illustrates theoretical evanescent surface field enhancement for SPR and TIR sensing according to the present invention.

FIG. 14 compares the evanescent field intensity in the sensing medium for SPR excitation and TIR excitation. Specifically, FIG. 14 illustrates theoretical evanescent surface field enhancement for SPR and TIR sensing: (a) SPR, (b) TIR, and (c) SPR reflectance response. FIG. 14 shows that using surface plasmons to intensify evanescent light results in a much larger evanescent field available to excite fluorescent labels. FIG. 14 also shows the characteristic surface plasmon resonance dip whose minimum corresponds to the maximum of the SPR evanescent field enhancement.

Figure 15:
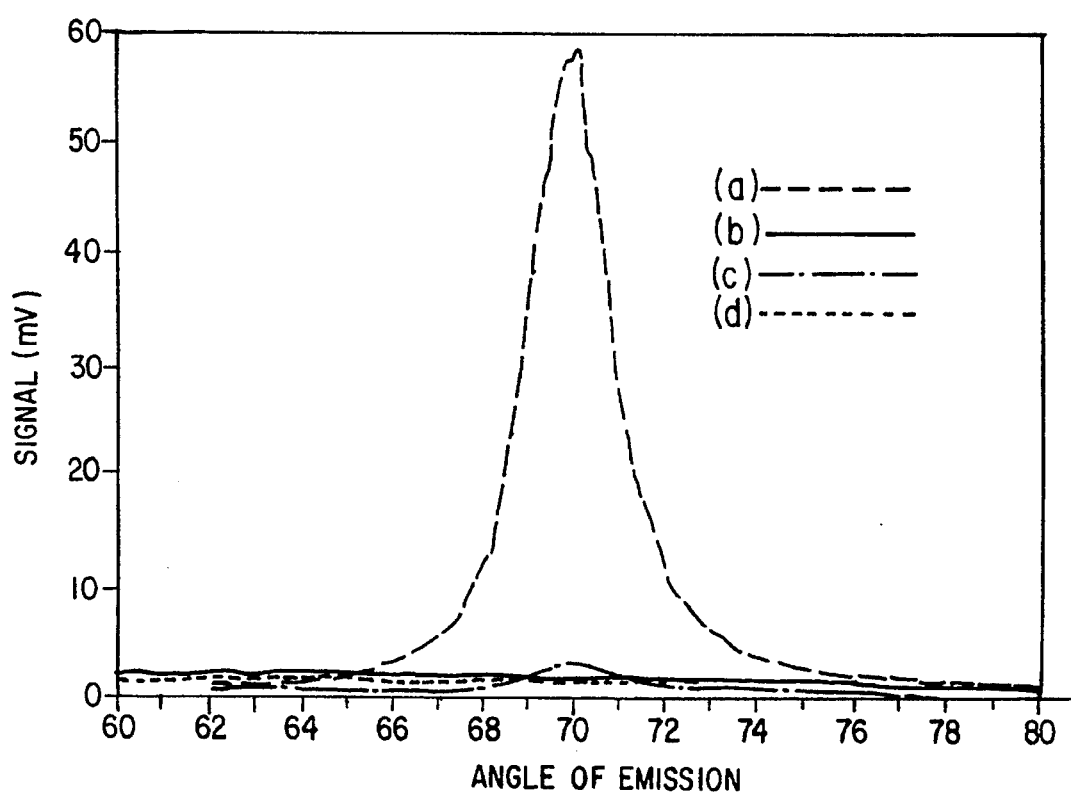
FIG. 15 illustrates emission responses of SPR and TIR fluorimmunoassay for hCG analyte according to the present invention.

The advantage of SPR enhanced fluorescence is most dramatically illustrated in FIG. 15, which compares the emission responses of SPR and TIR fluorimmunoassay for hCG analyte. FIG. 15 shows that SPR can significantly enhance signals for an evanescent biosensor. In particular, note that the signal intensities for 2500 mIU/ml hCG and 0 mIU/ml hCG are almost identical for the TIR sensor, while the SPR sensor exhibits a signal change of more than 55 mV. The simple optical format of the present invention allows straightforward implementation of this technique. Because of the large signal, sensitivity requirements for the detection electronics are reduced, so a simpler overall system is possible. Specifically, FIG. 15 illustrates a comparison of emission responses for SPR and TIR fluoroimmunoassay s for hCG in HEPES buffer: (a) SPR @2500 mIU/ml; (b) SPR @0 mIU/ml; (c) TIR @2500 mIU/ml; and (d) TIR @0 mIU/ml.

Figure 16:
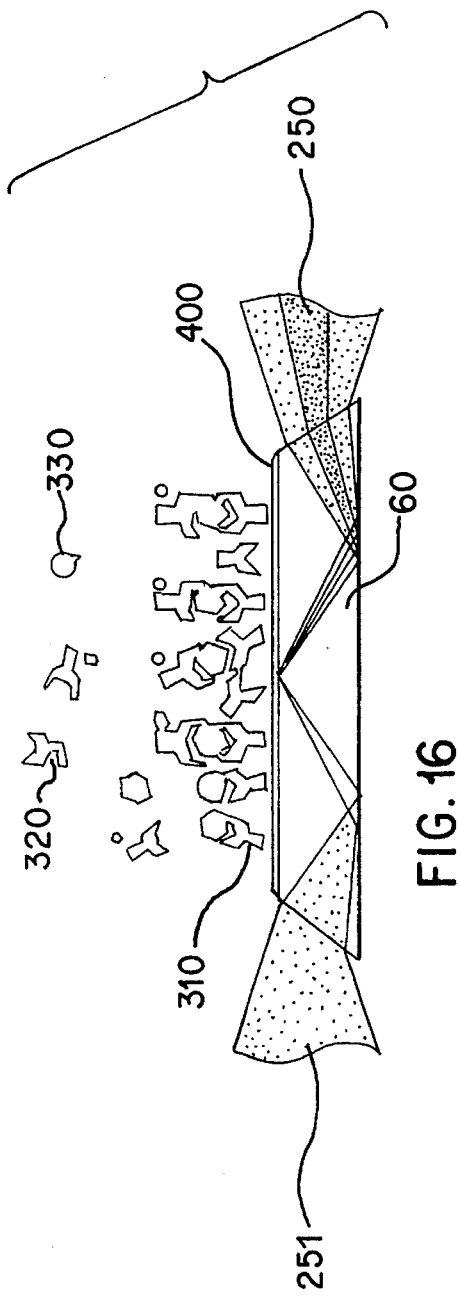
FIG. 16 illustrates a side view of a SPR enhanced fluorescent biosensor waveguide cartridge according to the present invention.

FIG. 16 illustrates a layout of a SPR enhanced fluorescent biosensor waveguide cartridge. Immobilized antibody, 310, is bound to metal film, 10. The focused beam, 251, is refracted when it enters the waveguide, 60. Antigen 330 binds to immobilized antibody, 310. Labelled antibody, 320, then binds to antigen 330. The dark band, 250, shown toward the right side of FIG. 16 corresponds to those rays that couple to the surface plasmon resonance and are thus attenuated. The angular position of dark band 250 provide reference signal information concerning the bioreactive layer and can be used to compensate for fluctuations and drift in the transverse magnetic polarized light source by detecting a change in the reference signal.

Figure 17:
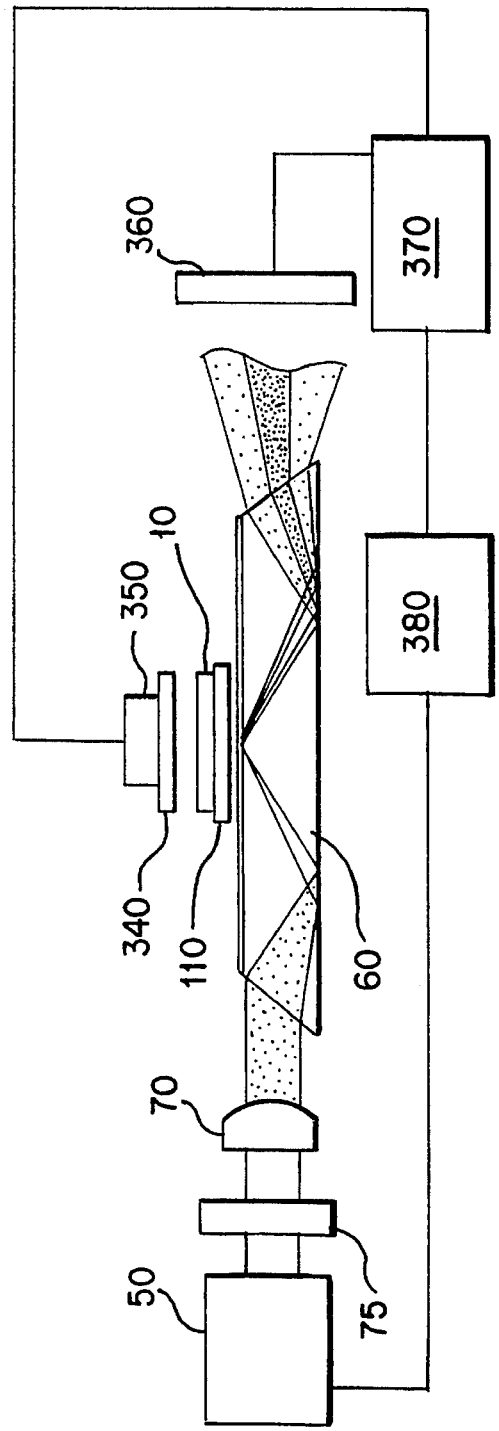
FIG. 17 illustrates a side view of an optical system used for surface plasmon resonance enhanced fluorescence detection according to the present invention.

FIG. 17 illustrates an optical system used for surface plasmon resonance enhanced fluorescence detection. FIG. 17 is a diagram of the optical detection system that monitors the state of the "indirect" waveguide biosensor cartridge diagrammed in FIG. 16 by surface plasmon resonance enhanced fluorescence (SPRF). TM-polarized light from a collimated laser diode, 50, is focused into the waveguide biosensor element by a cylindrical lens, 70. By so doing, a spectrum of angles are coupled into the waveguide with an angular halfwidth of about 1°–2°, determined by the surface plasmon resonance properties of the biosensing multilayer, 400, on the waveguide. This small angular width makes the system very insensitive to misalignment allowing a much coarser optical design than commonly possible with waveguide sensors. The light guided in the waveguide, 60, is coupled into surface plasmon polaritons (SPPs), which propagate at the interface between the metal film deposited on the waveguide and the biosensing layer. Because of this, the electric field of the laser diode light is highly concentrated in the biosensing multilayer, 400, above the metal film and excites fluorescent tags in the layer. In the example, fluorescent labels on antibodies are used in an immunoassay biochemical recognition layer. The format is also possible for nucleic acid probes. The fluorescent light then passes through an optical filter, 340, and is detected by a photodetector, 350, above the transparent sample injection flow cell, 110, on the biosensor. Because the metal film also acts as a mirror to reflect fluorescence up toward the detector, an added increase in signal is achieved with our design. Alternate configurations are possible where the fluorescent light is coupled into the substrate-mode waveguide cartridge to a different photodetector.

Laser light that is not absorbed by the biosensing layer travels down the waveguide to a second photodetector, 360. The output of this photodetector is used as a reference signal, by which the output of the fluorescence-detecting photosensor is ratioed by lockin ratio detector, 370, which is connected to modulator source driver, 380. Thus, fluctuations and drift in the laser diode source, 50, can be automatically compensated.

There are several reasons why SPRF biosensors are superior to conventional systems in which the labeled biosensitive layer is illuminated by a direct beam from the excitation source. First, shining light directly on the layer can excite remanent fluorescent markers in solution that did not tag any particular molecule. Thus, direct illumination could result in overestimates of the amount and types of analyte present, or even false alarms. By using an evanescent field approach, the excitation field is limited to the thin biosensing layer and does not excite fluorescence in the volume above the film. Perhaps even more significant, the surface plasmon evanescent wave phenomenon essentially intensifies the light in the biosensing layer so that much larger signals are possible than with direct illumination of light from the same laser diode source. This dramatically increases sensitivity and reduces the sophistication required of the detection electronics. The third reason is that, by virtue of our waveguide design, the excitation light never directly impinges on the detector. Only a small amount of excitation light scattered at the biosensor interface escapes the surface of the waveguide, and this light is easily removed by the filter.

The foregoing descriptions of preferred embodiments are provided by way of illustration. Practice of the present invention is not limited thereto and variations therefrom will be readily apparent to the skilled without deviating from the spirit of the present invention.

Since the optical detection technology is generic, it can be applied to a wide variety of both immunological and nucleic acid probe biochemistries developed to sense viral, bacterial, and antigenic components associated with infectious diseases such as HIV, tuberculosis, infectious hepatitis (of all types), Lyme disease, cervical cancer (caused by papilloma virus), etc. Of particular interest will be sensor chemistries that presently require ELISA for analysis, which typically takes several days to process. The present, compact, portable invention will find use in both research and clinical diagnostics and will require minimal operator skill to perform reliable tests. Because of its ease of use and its potential low cost, the present invention could even find use in doctor's offices for routine screening of infectious diseases. Spin-off applications to non-biomedical areas abound: environmental monitoring, chemical process control, biotechnology, and occupational safety monitoring all would benefit from the availability of sensitive, uncomplicated, on-site, real-time environmental chemical detection.

While there is shown and described herein certain specific combinations embodying this invention for the purpose of clarity of understanding, the same is to be considered as illustrative in character, it being understood that only preferred embodiments have been shown and described. It will be manifest to those skilled in the art that certain changes, various modifications and rearrangements of the parts may be made without departing from the spirit and scope of the underlying inventive concept and that the same is not limited to the particular forms herein shown and described except insofar as indicated in the scope of the appended claims.

The entirety of everything cited above or below is expressly incorporated herein by reference.

REFERENCES

1. Raether, H., Surface Plasmons on Smooth and Rough Surfaces and on Gratings, Springer-Verlag, Berlin (1988).

2. Hage, D. S. "Immunoassays," Anal. Chem., 63(12), (1991), pages 206R–209R.

3. Sadowski, J. W., "Review of Optical Methods in Immunosensing," SPIE Proc. Vol. 954, pages 413–419 (1988).

4. Pharmacia Biacore™ product brochure.

5. ICN Immunobiologicals Catalog, May 1992, pages 732–735.

6. Harlow, E. and D. Lane, Antibodies: A Laboratory Manual, Cold Spring Harbor Laboratory, Cold Spring Harbor (1988).

7. Wolfbeis, O., ed., Fiber Optic Chemical Sensors and Biosensors, Volume II, CRC Press, Boston, (1991), 217–257.

8. Kwok, S., D. H. Mack, K. B. Mullins, B. Poiesz, G. Ehrlich, D. Blair, A. Friedman-Kien, and J. J. Sninsky "Identification of Human Immunodeficiency Virus Sequences by Using In Vitro Enzymatic Amplification and Oligmer Clevage Detection," J. Virol., 61, (1987), pages 1690–1694.

9. Pollard-Knight, D. et al., "Immunoassays and Nucleic Acid Detection with a Biosensor Based on Surface Plasmon Resonance," Ann. Biol. Clin., 48, 1990, pages 642–646.

10. Golden, J. P. et al, "Fluorometer and Tapered Fiber Optic Probes for Sensing in the Evanescent Wave," Opt. Eng., 31(7), 1992, pages 1458–1462.

11. Lambeck, P. V., "Integrated Opto-Chemical Sensors," Sens. Actu. B, 8, 1992, pages 103–116.

12. Mujumdar, R. B., et al., Cytometry, 10, 1989, pages 11–19.

13. Ernst, L. A., et al., Cytometry, 10, 1989, pages 10–13.

14. Southwick, P. L., et al., Cytometry, 11, 1990, pp. 418–430.

15. Attridge, J. W., et al. "Sensitivity Enhancement of Optical Immunosensors by the Use of a Surface Plasmon Resonance Fluoroimmunoassay, "Biosensors. & Bioelect., 6, 1991, pages 201–214.

16. Daneshvar, M. I., "Investigation of a Near-Infrared Fiber Optic Immunosensor," Proceedings SPIE, 2068, "Chemical, Biochemical, and Environmental Sensors V," R. A. Lieberman (ed), 1993, pages 128–138.

17. Eduardo Fontana, R. H. Pantell and Samuel Strober, Surface plasmon immunoassay, Applied Optics, Vol. 29, No. 31, pages 4694–4704, (1 Nov. 1990).

18. Bo Liedberg, Claes Nylander and Ingemar Lundstrom, Surface Plasmon resonance for gas detection and biosensing, Sensors and Actuators, 4, pages 299–304 (1983).

19. Morgan, H. and D. M. Taylor, "A Surface Plasmon Resonance Immunosensor Based on the Streptavidin-Biotin Complex," Biosens. & Bioelect., 7, (1992), pages 405–410.

20. Taylor, D. M., et al,. "Characterization of Chemisorbed Monolayers by Surface Potential Measurements," J. Phys, D:Appl. Phys., 124, (1991), pages 443–450.

21. Kobayashi, J. and Y. Ikada, "Covalent Immobilization of Proteins Onto the Surface of Poly(vinyl alcohol) Hydrogel," Biomaterials, 12, (1991), pages 747–751.

22. Johnsson, B. et al, "Immobilization of Proteins to a Carboxymethyldextran-Modified Gold Surface for Biospecific Interaction Analysis in Surface Plasmon Resonance Sensors," Anal. Biochem., 196, (1991), 268–277.

23. Lofas, S. and B. Johnsson, "A Novel Hydrogel Matrix on Gold Surfaces in Surface Plasmon Resonance Sensors for Fast and Efficient Covalent Immobilization of Ligands," J. Chem. Soc. Commun., (1990), pages 1526–1528.

What is claimed is:

1. A surface plasmon resonance sensor comprising:
   a substrate-mode metal film coated waveguide cartridge comprising:
      a planar waveguide including a plurality of reflector surfaces within the planar waveguide; and
      a metal film deposited directly on the planar waveguide, the metal film and the planar waveguide defining a plasmon resonance interface directly on the planar waveguide;
   a sample flow cell adjacent the substrate-mode metal film coated waveguide cartridge;
   a transverse magnetic polarized light source optically connected to the planar waveguide;
   a cylindrical diverging lens optically connected to the planar waveguide; and
   a detector array comprising a plurality of photodetectors optically connected to the cylindrical diverging lens.

2. The surface plasmon resonance sensor of claim 1, wherein
   the planar waveguide comprises:
      a first face;
      a second face that is substantially parallel to the first face;
      a first edge that is substantially perpendicular to both the first face and the second face;
      a second edge that is substantially parallel to the first edge and substantially perpendicular to both the first face and the second face;
      a first angled edge; and
      a second angled edge,
   the metal film is deposited directly on the first parallel face of the planar waveguide,
   the transverse magnetic polarized light source is optically connected to the first angled edge of the planar waveguide, and
   the cylindrical diverging lens is optically connected to the second angled edge of the planar waveguide.

3. The surface plasmon resonance sensor of claim 1, wherein the substrate-mode metal film coated waveguide cartridge further comprises a plurality of channels comprising a reference channel and the plurality of photodetectors comprises a two dimensional array of photodetectors.

4. The surface plasmon resonance sensor of claim 1, further comprising an optical filter adjacent and optically connected to the sample flow cell and a fluorescence photodetector array adjacent, and optically connected to, the optical filter.

5. The surface plasmon resonance sensor of claim 1, wherein the metal film comprises silver.

6. The surface plasmon resonance sensor of claim 1, wherein the metal film comprises gold.

7. The surface plasmon resonance sensor of claim 1, wherein the transverse magnetic polarized light source comprises a collimated laser diode module, a polarizer and a cylindrical focusing lens.

8. A method of sensing the presence or absence of a compound of interest using a surface plasmon resonance sensor comprising:
   providing a surface plasmon resonance sensor comprising:
      a substrate-mode metal film coated waveguide cartridge comprising:
         a planar waveguide including a plurality of reflector surfaces within the planar waveguide; and
         a metal film coated on the planar waveguide, the metal film and the planar waveguide defining a plasmon resonance interface directly on the planar waveguide;
      a sample flow cell adjacent the substrate-mode metal film coated waveguide cartridge;
      a transverse magnetic polarized light source optically connected to the planar waveguide;
      a cylindrical diverging lens optically connected to the planar waveguide; and
      a detector array comprising a plurality of photodetectors optically connected to the cylindrical diverging lens;
   transmitting light rays from the transverse magnetic polarized light source into the planar waveguide;
   monitoring an intensity of light rays from the planar waveguide through the cylindrical diverging lens with the detector array so as to locate a position of a surface plasmon resonance attenuated light band on the detector array;
   introducing a sample into the sample flow cell; and
   sensing the presence or absence of the compound of interest in the sample by detecting a translation of the position of the surface plasmon resonance attenuated light band as a shift in the position of the surface plasmon resonance attenuated band on the detector array.

9. The method of claim 8, further comprising introducing an activating buffer into the sample flow cell.

10. The method of claim 8, further comprising
    monitoring an intensity of light rays from a reference channel of the planar waveguide through the cylindrical diverging lens with the detector array so as to locate a position of a reference surface plasmon resonance attenuated light band on the detector array; and
    comparing the translation of the position of the surface plasmon resonance attenuated light band to a translation of a position of the reference surface plasmon resonance attenuated light band as a shift in the position of the reference surface plasmon resonance attenuated band on the detector array,
    wherein the substrate-mode metal film coated waveguide cartridge further comprises a plurality of channels comprising the reference channel and the plurality of photodetectors comprises a two dimensional array of detectors.

11. A method of sensing the presence or absence of a compound of interest using a surface plasmon resonance enhanced fluorescence sensor comprising:
    providing a surface plasmon resonance enhanced fluorescence sensor comprising:
       a substrate-mode metal film coated waveguide cartridge comprising:
          a planar waveguide including a plurality of reflector surfaces within the planar waveguide; and
          a metal film coated on the planar waveguide, the metal film and the planar waveguide defining a plasmon resonance interface directly on the planar waveguide;
       a sample flow cell adjacent the substrate-mode metal film coated waveguide cartridge;
       an optical filter adjacent, and optically connected to, the sample flow cell;
       a fluorescence photodetector array adjacent, and optically connected to, the optical filter;
       a transverse magnetic polarized light source optically connected to the planar waveguide;

a cylindrical diverging lens optically connected to the planar waveguide; and a detector array comprising a plurality of photodetectors optically connected to the planar waveguide;

transmitting light rays from the transverse magnetic polarized light source into the planar waveguide;

monitoring an intensity of light rays from the planar waveguide through the cylindrical diverging lens with the detector array so as to obtain a reference signal;

monitoring an intensity of light from the sample flow cell through the optical filter with the fluorescence photodetector array so as to obtain a reference value for an initial level of fluorescence;

introducing a sample comprising a fluorescent label into the sample flow cell;

compensating for fluctuations and drift in the transverse magnetic polarized light source by detecting a change in the reference signal; and sensing the presence or absence of the compound of interest in the sample by detecting a change in the initial level of fluorescence.

12. The method of claim 11, further comprising introducing an activating buffer into the sample flow cell.

13. The surface plasmon resonance sensor of claim 1, further comprising a mirror optically connected between said cylindrical diverging lens and said detector array.

14. The surface plasmon resonance sensor of claim 1, wherein said transverse magnetic polarized light source comprises a laser, said laser defining an axis of said transverse magnetic polarized light source that is within a plane defined by said planar waveguide.

15. The surface plasmon resonance sensor of claim 1, wherein said metal film is part of a metal film/immunoassay biolayer that is deposited directly on top of said planar waveguide.

16. The surface plasmon resonance sensor of claim 4, wherein a spectrum of angles are coupled into said planar waveguide, said spectrum of angles having an angular halfwidth of from approximately 1° to approximately 2°.

17. The method of claim 8, wherein said metal film is part of a metal film/immunoassay biolayer that is deposited directly on top of said planar waveguide.

18. The method of claim 8, wherein an angular bandwidth of coupled light inside said planar waveguide is approximately 10°.

19. The method of claim 11, wherein said metal film is part of a metal film/immunoassay biolayer that is deposited directly on top of said planar waveguide.

20. The method of claim 11, wherein a spectrum of angles are coupled into said planar waveguide, said spectrum of angles having an angular halfwidth of from approximately 1° to approximately 2°.

* * * * *